(12) United States Patent
Mobley

(10) Patent No.: US 6,168,088 B1
(45) Date of Patent: Jan. 2, 2001

(54) AIR FRESHENER CARD, METHOD OF USE AND METHOD OF MANUFACTURE

(76) Inventor: David Mobley, 7925 Kristina La., Ft. Worth, TX (US) 76180

( * ) Notice: Under 35 U.S.C. 154(b), the term of this patent shall be extended for 0 days.

(21) Appl. No.: 09/326,622

(22) Filed: Jun. 7, 1999

(51) Int. Cl.⁷ .................... A61L 9/04; A24F 25/00
(52) U.S. Cl. ................. 239/6; 239/34; 239/53; 239/54; 422/5; 428/905; 512/1; 512/2; 512/3
(58) Field of Search .................. 239/6, 34, 53, 239/54, 55, 56, 289; 422/5, 124, 305; 512/1–4; 428/34.2, 905

(56) References Cited

U.S. PATENT DOCUMENTS

| | | | |
|---|---|---|---|
| 2,120,204 | * 6/1938 | Langhorst | 239/54 |
| 2,303,073 | * 11/1942 | Brown | 239/53 |
| 3,575,345 | * 4/1971 | Buck, Jr. | 239/34 |
| 4,314,299 | 2/1982 | Ishida et al. | 360/130.33 |
| 4,802,626 | 2/1989 | Forbes et al. | 239/36 |
| 4,809,912 | * 3/1989 | Santini | 239/57 X |
| 4,889,755 | * 12/1989 | Charbonneau | 239/34 X |
| 4,952,400 | * 8/1990 | Tararuj et al. | 428/321.5 X |
| 5,372,303 | 12/1994 | Paul | 239/56 |
| 5,395,047 | 3/1995 | Pendergrass, Jr. | 239/56 |
| 5,419,879 | * 5/1995 | Vlahakis et al. | 422/305 |
| 5,497,942 | 3/1996 | Zingle et al. | 239/6 |
| 5,503,332 | * 4/1996 | Glenn | 239/34 X |
| 5,518,790 | 5/1996 | Huber et al. | 428/35.2 |
| 5,585,343 | * 12/1996 | McGee et al. | 512/2 X |
| 5,611,486 | 3/1997 | Paul | 239/56 |
| 5,782,409 | 7/1998 | Paul | 239/56 |
| 5,804,299 | 9/1998 | Nakata et al. | 428/334 |
| 5,876,678 | * 3/1999 | Harrell et al. | 239/53 X |
| 6,012,643 | * 1/2000 | Barlow et al. | 239/6 |

* cited by examiner

Primary Examiner—Andres Kashnikow
Assistant Examiner—Steven J. Ganey

(57) ABSTRACT

A method for applying air freshener within an automobile is disclosed. The method includes the steps of retrieving an air freshener card, locating a substantially hidden position within the automobile, and placing the air freshener card at the substantially hidden position. An air freshener card and method for making the same is also disclosed.

6 Claims, 1 Drawing Sheet

AIR FRESHENER CARD, METHOD OF USE AND METHOD OF MANUFACTURE

BACKGROUND OF THE INVENTION

1. Field of the Invention

The invention relates to methods for applying air freshener within an automobile. The invention further relates to air fresheners and a dispensing assembly useful in performing the present method.

2. Description of the Prior Art

It has been common practice for many years to apply air freshener, or fragrance, within automobiles at carwashes and detailing centers. The air freshener is generally applied to freshen the smell within the automobile interior and lasts for approximately 1–2 days.

Air freshener is currently applied in liquid form and is generally sprayed under the seat of an automobile. Unfortunately, many operators applying the liquid air freshener are not very careful and the liquid air freshener often ends up on various undesirable potions of the automobile. For example, the liquid air freshener sometimes ends up on the dashboard of the automobile, where the liquid air freshener interacts with the plastic material of the dashboard to destroy the dashboard. When this occurs, the damage to the dashboard is irreparable and the only alternative is to replace the entire affected dashboard. The liquid air freshener also is inadvertently sprayed upon other undesirable portions of automobile interiors, necessitating costly repair and/or replacement of the damaged components.

The cost of replacing and repairing automobile interiors damaged by improperly applied liquid air freshener is generally borne by the owner of the carwash or detailing center and/or the manufacturing company for the liquid air freshener. As such, a great incentive exists to obviate the problem.

Training of employees helps in limiting the occurrence of damage to automobile interiors. However, training provides only limited success.

In addition to damaging automobile interiors, the formulation commonly employed with liquid air fresheners disperses the fragrance in an undesirable manner. For example, one known formulation includes approximately 80% by weight water, 10% by weight alcohol, 5–6% by weight surfactant, and 4–5% fragrance oil. The alcohol carrier of the formulation quickly vaporizes after the initial application and creates a very strong, often overwhelming, initial fragrance which rapidly diminishes thereafter.

Some operators may choose to use hanging air freshener hung from the rearview mirror of an automobile. Many people, however, find these air freshener cards distracting and/or unsightly, and choose not to use them within an automobile. In addition, the cost of providing hanging air fresheners is prohibitive when compared with the cost of simply spraying liquid air freshener. Specifically, the wholesale cost of hanging air fresheners is currently approximately $.50, while a sprayed liquid air freshener application generally costs the carwash or detailing center less than $0.06.

The use of hanging air fresheners in this manner is also undesirable from a marketing point of view. The fragrance from sprayed liquid air fresheners generally last a day or two, while the fragrance from hanging air freshener generally lasts two to three weeks. If hanging air freshener where used as a replacement for sprayed liquid air freshener, countertop sales of hanging air fresheners would certainly decrease.

As such, a need exists for a convenient and reliable method for discretely applying air freshener to the interior of an automobile. The present invention provides such a method.

SUMMARY OF THE INVENTION

It is, therefore, an object of the present invention to provide a method for applying air freshener within an automobile. The method includes the steps of retrieving an air freshener card, locating a substantially hidden position within the automobile, and placing the air freshener card at the substantially hidden position.

It is also an object of the present invention to provide a method wherein the substantially hidden position is under a seat of the automobile.

It is another object of the present invention to provide a method wherein the substantially hidden position is under a front seat of the automobile.

It is a further object of the present invention to provide a method wherein the air freshener card is a piece of cardboard impregnated with liquid air freshener such that the liquid fragrance is substantially bound to the cardboard and will not leach therefrom.

It is also an object of the present invention to provide a method for preparing a plurality of air freshener cards. The method is achieved by placing a predetermined number of cards within a container, pouring a predetermined quantity of an air freshener formulation into the container, and sealing the container and allowing the air freshener formulation to saturate the cards.

It is another object of the present invention to provide a method wherein the cards are cardboard.

It is a further object of the present invention to provide a method wherein the air freshener formulation is composed of fragrance oil and hexylene glycol.

It is also an object of the present invention to provide a method wherein the air freshener formulation is composed of approximately 80–85% fragrance oil and 15–20% hexylene glycol.

It is another object of the present invention to provide a method wherein approximately 0.026 ounces of air freshener formulation is poured within the container for each card placed within the container.

It is a further object of the present invention to provide a method wherein approximately 250 cards and 6 M ounces of the air freshener formulation are placed within the container prior to sealing.

It is also an object of the present invention to provide an air freshener card including a substrate of cardboard impregnated with an air freshener formulation composed of fragrance oil and hexylene glycol.

It is another object of the present invention to provide an air freshener card wherein the cardboard is 100 lb. weight cardboard.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiment of the present invention is disclosed herein. It should be understood, however, that the disclosed embodiment is merely exemplary of the invention, which may be embodied in various forms. Therefore, the details disclosed herein are not to be interpreted as limited, but merely as the basis for the claims and as a basis for teaching one skilled in the art how to make and/or use the invention.

Figure 1:
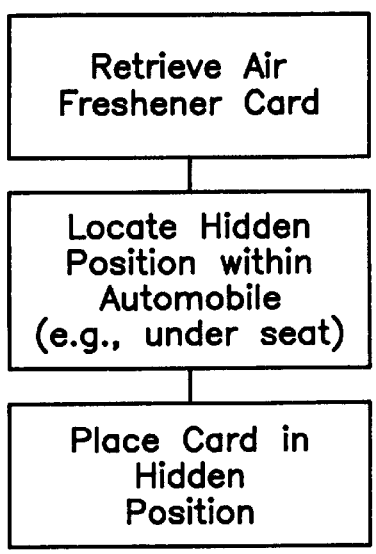
FIG. 1 is a flowchart of the steps taken in accordance with the present invention.
Figure 2:
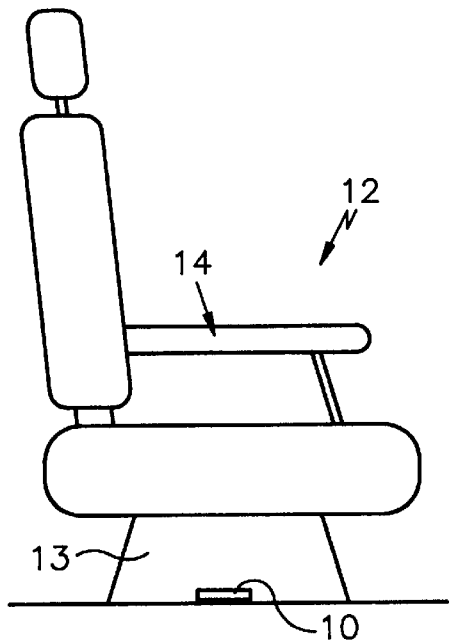
FIG. 2 is a side view of an automobile with an air freshener card placed under the car seat in accordance with the present invention.

With reference to FIGS. 1 and 2, the steps associated with the present method for applying air freshener within an automobile 12 are disclosed. In accordance with the invention, a non-liquid air freshener card 10 is applied within an automobile.

The present method allows operators of carwashes and automobile detailing shops to apply air fresheners within an automobile 12 without worrying that the applied air freshener will cause damage to the interior of the automobile 12.

The operator first retrieves an air freshener card 10. The card 10 is preferably a piece of cardboard impregnated with liquid air freshener such that the liquid fragrance is substantially bound to the cardboard and will not leach therefrom. In accordance with the present invention the air freshener formulation is composed of approximately 80–85% fragrance oil and 15–20% hexylene glycol. The air freshener formulation is saturated in a cardboard substrate in a manner discussed below in greater detail. As those skilled in the art will also appreciate, the present invention is not limited to specific air freshener fragrances, and a wide variety of fragrances may be used without departing from the spirit of the present invention.

The cardboard is preferably 100 lb. weight performance blotter manufactured by Crown Vantage, although other materials may be used without departing from the spirit of the invention.

The cardboard is preferably cut into approximately 2" square cards, although other size squares may be used without departing from the spirit of the present invention.

The combination of the air freshener formulation and the cardboard provide an ideal uniform release of the fragrance over the period of 3 to 4 days. As those skilled in the art will readily appreciate, variations in the formulation and cardboard may be made to suit specific applications without departing from the spirit.

The air freshener formulation is ideally suited for application to the cardboard employed in accordance with the preferred embodiment of the present invention. The cards are impregnated by placing a plurality of cards within a container 16, pouring a predetermined quantity of the air freshener formulation into the container 16 and closing the container for approximately 1 day. During this time, the cards absorbed the air freshener formulation and are ready for use.

In accordance with the preferred embodiment of the present invention, approximately 250 cards are placed within the container 16 and 6½ ounces of the air freshener formulation is poured into the container. The container 16 is then sealed and allowed to sit for a predetermined period of time, for example, 1 day. During this time, the air freshener evenly distributes itself amongst the cards to produce 250 uniformly saturated air freshener cards. The impregnated cards 10 may be shipped for use within the same container 16 and no further processing is required.

Once an air freshener card 10 is retrieved, the operator locates a substantially hidden position within the automobile 12. In accordance with the preferred embodiment of the present invention, the best location is under 13 the front seat 14 of the automobile 12. Positioning the air freshener card under the seat of an automobile 12 is considered ideal in accordance with the present invention. Specifically, by placing the air freshener card 10 under the seat 14, the air freshener card 10 is completely out of sight and substantially hidden from small children. In addition, the operator of the carwash or detailing center need not enter the automobile 12 to place the air freshener card 10 in position.

The air freshener card 10 is then placed at the substantially hidden position, and the process is complete. As discussed above, because liquid air freshener is not sprayed in accordance with the present invention, there is no fear that the air freshener will be inadvertently sprayed upon an interior surface of an automobile not compatible with the air freshener.

In addition, the air freshener card 10 is hidden and, therefore, nt visible or distracting to the owner of the automobile.

Figure 3:
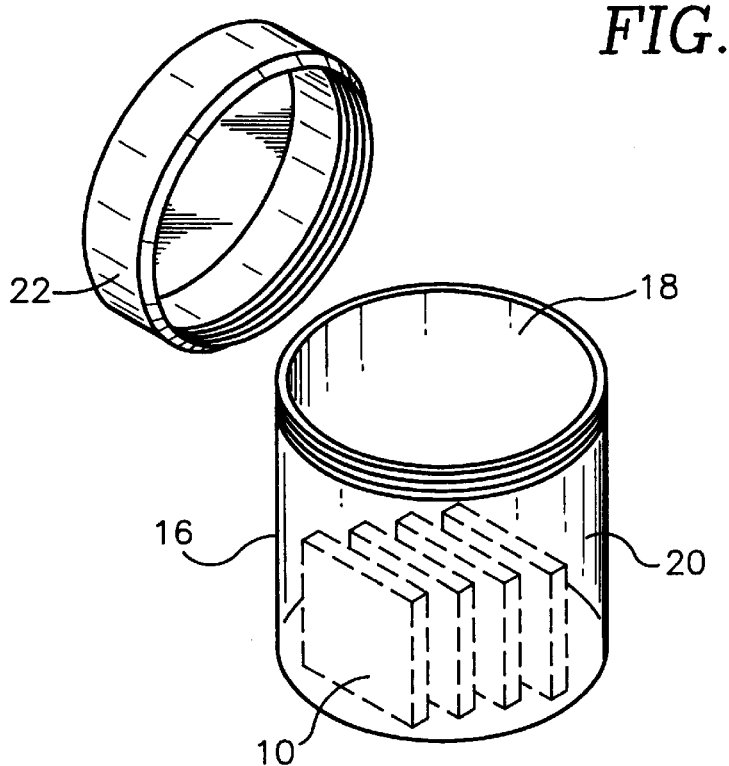
FIG. 3 is a perspective view of the container used in accordance with the present invention.

Retrieval, manufacture and shipping of the air freshener cards 10 used in accordance with the present invention is facilitated by providing an air freshener card dispensing container 16 as shown in FIG. 3. The container is substantially airtight and includes an access opening 18 providing access to an interior cavity 20 of the container 16.

The access opening 18 is selectively sealed by a screw on cover 22 shaped and dimensioned to selectively seal the access opening 18. While a screw on cover is disclosed in accordance with the preferred embodiment of the present invention, the cap may be sealed in a variety of ways, for example, flip top cap or snap on cap, without departing from the spirit of the present invention.

A plurality of air freshener cards 10 are stored within the container 16 for ready retrieval by the operator of the carwash or detailing center.

While the preferred embodiments have been shown and described, it will be understood that there is no intent to limit the invention by such disclosure, but rather, is intended to cover all modifications and alternate constructions falling within the spirit and scope of the invention as defined in the appended claims.

What is claimed is:

1. A method for applying air freshener within an automobile, comprising:
retrieving an air freshener card, the air freshener card including a substrate of cardboard impregnated with a liquid air freshener formulation composed of approximately 80–85% fragrance oil and 15–20% hexylene glycol to provide a uniform release of the air freshener formulation;
locating a substantially hidden position within the automobile; and
placing the air freshener card at the substantially hidden position.

2. The method according to claim 1, wherein the substantially hidden position is under a seat of the automobile.

3. The method according to claim 1, wherein the substantially hidden position is under a front seat of the automobile.

4. The method according to claim 1, wherein the air freshener card is a piece of cardboard impregnated with a liquid fragrance such that the liquid fragrance is substantially bound to the cardboard and will not leach therefrom.

5. The method according to claim 1, wherein the cardboard is 100 lb. weight cardboard.

6. The method according to 1, wherein the air frashener card is impregnated with approximately 0.026 ounces of the air freshener formulation.

* * * * *